(12) United States Patent
Yassinzadeh

(10) Patent No.: US 7,815,640 B2
(45) Date of Patent: Oct. 19, 2010

(54) APPARATUS AND METHODS FOR CLOSING VASCULAR PENETRATIONS

(75) Inventor: Zia Yassinzadeh, San Jose, CA (US)

(73) Assignee: Cardiva Medical, Inc., Sunnyvale, CA (US)

( * ) Notice: Subject to any disclaimer, the term of this patent is extended or adjusted under 35 U.S.C. 154(b) by 448 days.

(21) Appl. No.: 11/943,882

(22) Filed: Nov. 21, 2007

(65) Prior Publication Data

US 2008/0065064 A1    Mar. 13, 2008

Related U.S. Application Data

(62) Division of application No. 10/795,019, filed on Mar. 3, 2004, now Pat. No. 7,322,976.

(60) Provisional application No. 60/452,037, filed on Mar. 4, 2003.

(51) Int. Cl.
*A61B 18/14* (2006.01)
(52) U.S. Cl. ........................................................ 606/50
(58) Field of Classification Search ............... 606/34, 606/37, 40–43, 46, 49, 50, 213
See application file for complete search history.

(56) References Cited

U.S. PATENT DOCUMENTS

| 4,929,246 | A | 5/1990 | Sinofsky |
| 5,061,274 | A | 10/1991 | Kensey |
| 5,108,420 | A | 4/1992 | Marks |
| 5,197,971 | A | 3/1993 | Bonutti |
| 5,258,000 | A | 11/1993 | Gianturco |
| 5,290,552 | A | 3/1994 | Sierra et al. |
| 5,292,332 | A | 3/1994 | Lee |
| 5,383,896 | A | 1/1995 | Gershony et al. |
| 5,415,657 | A | 5/1995 | Taymor-Luria |
| 5,454,833 | A | 10/1995 | Boussignac et al. |
| 5,456,667 | A | 10/1995 | Ham et al. |
| 5,486,195 | A | 1/1996 | Myers et al. |
| 5,507,744 | A | 4/1996 | Tay et al. |
| 5,782,860 | A | 7/1998 | Epstein et al. |
| 5,810,810 | A | 9/1998 | Tay et al. |
| 5,851,210 | A | 12/1998 | Torossian |
| 5,861,003 | A | 1/1999 | Latson et al. |
| 5,895,398 | A | 4/1999 | Wensel et al. |
| 5,922,009 | A | 7/1999 | Epstein et al. |
| 5,951,589 | A | 9/1999 | Epstein et al. |

(Continued)

FOREIGN PATENT DOCUMENTS

WO    WO 92/22252    12/1992

(Continued)

*Primary Examiner*—Kevin T Truong
(74) *Attorney, Agent, or Firm*—Townsend and Townsend and Crew LLP

(57) ABSTRACT

Apparatus for sealing vascular penetrations comprise a shaft having an electrode or other energy-applying element at a distal end. The shaft is placed in a tissue tract over a blood vessel penetration and located using a locator which engages an inner wall of the blood vessel. Once in position, an anchor is used to hold the shaft, allowing the locator to be removed. Energy is then applied through a distal tip of the shaft in order to induce desiccation and plug formation in a blood pool formed between the distal end of the shaft and the wall of the blood vessel.

9 Claims, 9 Drawing Sheets

U.S. PATENT DOCUMENTS

| | | | |
|---|---|---|---|
| 6,012,457 | A | 1/2000 | Lesh |
| 6,045,570 | A | 4/2000 | Epstein et al. |
| 6,056,769 | A | 5/2000 | Epstein et al. |
| 6,056,770 | A | 5/2000 | Epstein et al. |
| 6,071,300 | A | 6/2000 | Brenneman et al. |
| 6,077,261 | A | 6/2000 | Behl et al. |
| 6,080,182 | A | 6/2000 | Shaw et al. |
| 6,146,396 | A | 11/2000 | Konya et al. |
| 6,248,124 | B1 | 6/2001 | Pedros et al. |
| 6,712,812 | B2 | 3/2004 | Roschak et al. |
| 6,913,614 | B2 | 7/2005 | Marino et al. |
| 7,025,776 | B1 | 4/2006 | Houser et al. |
| 7,115,127 | B2 | 10/2006 | Lindenbaum et al. |
| 7,223,266 | B2 * | 5/2007 | Lindenbaum et al. .......... 606/49 |
| 7,361,183 | B2 * | 4/2008 | Ginn .......................... 606/213 |
| 7,691,127 | B2 * | 4/2010 | Yassinzadeh ................ 606/213 |
| 2002/0072767 | A1 | 6/2002 | Zhu |
| 2003/0191493 | A1 | 10/2003 | Epstein et al. |

FOREIGN PATENT DOCUMENTS

| | | |
|---|---|---|
| WO | WO 95/05121 | 2/1995 |
| WO | WO 96/24290 | 8/1996 |
| WO | WO 98/34546 | 8/1998 |
| WO | WO 98/40017 | 9/1998 |
| WO | WO 00/06029 | 2/2000 |
| WO | WO 00/06031 | 2/2000 |

* cited by examiner

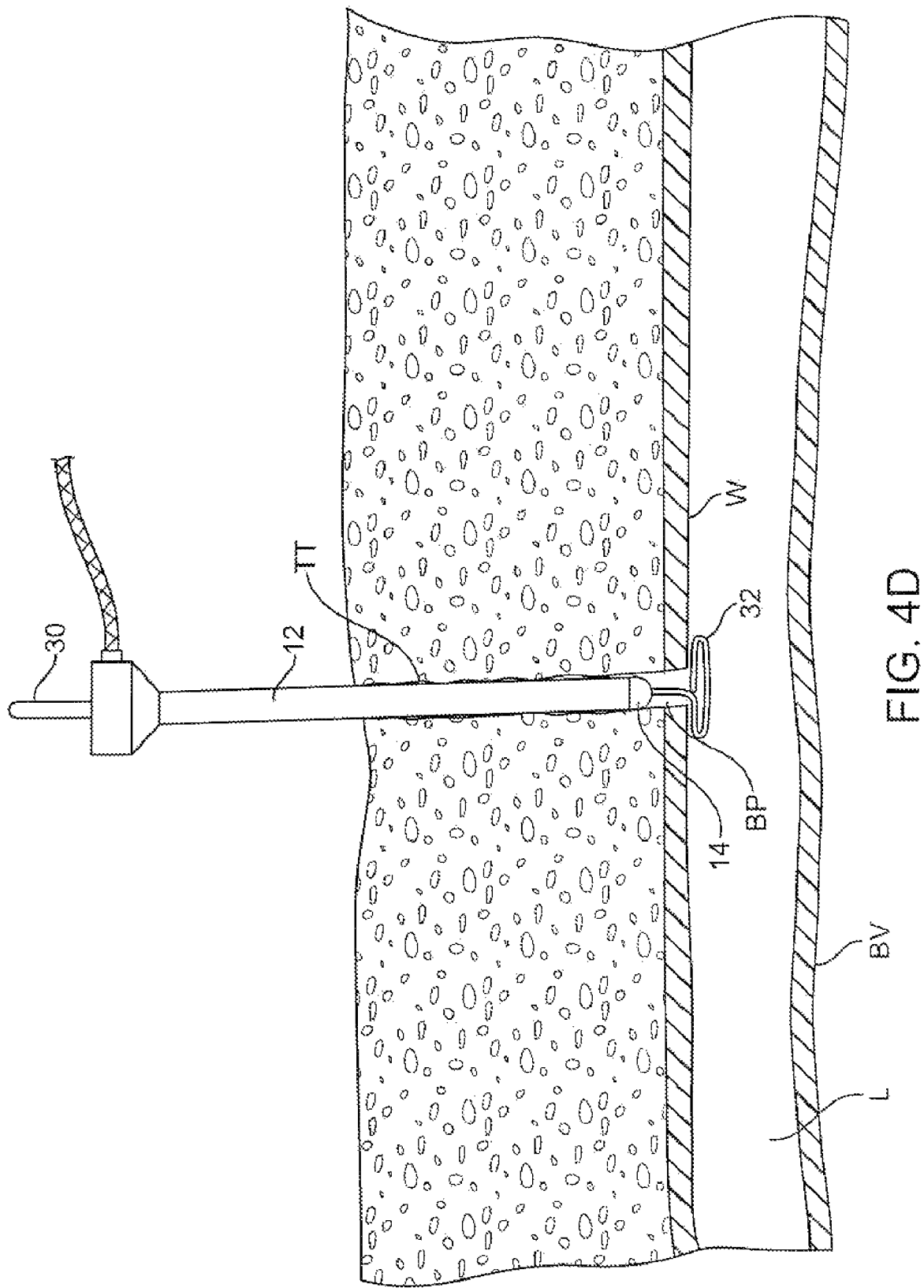

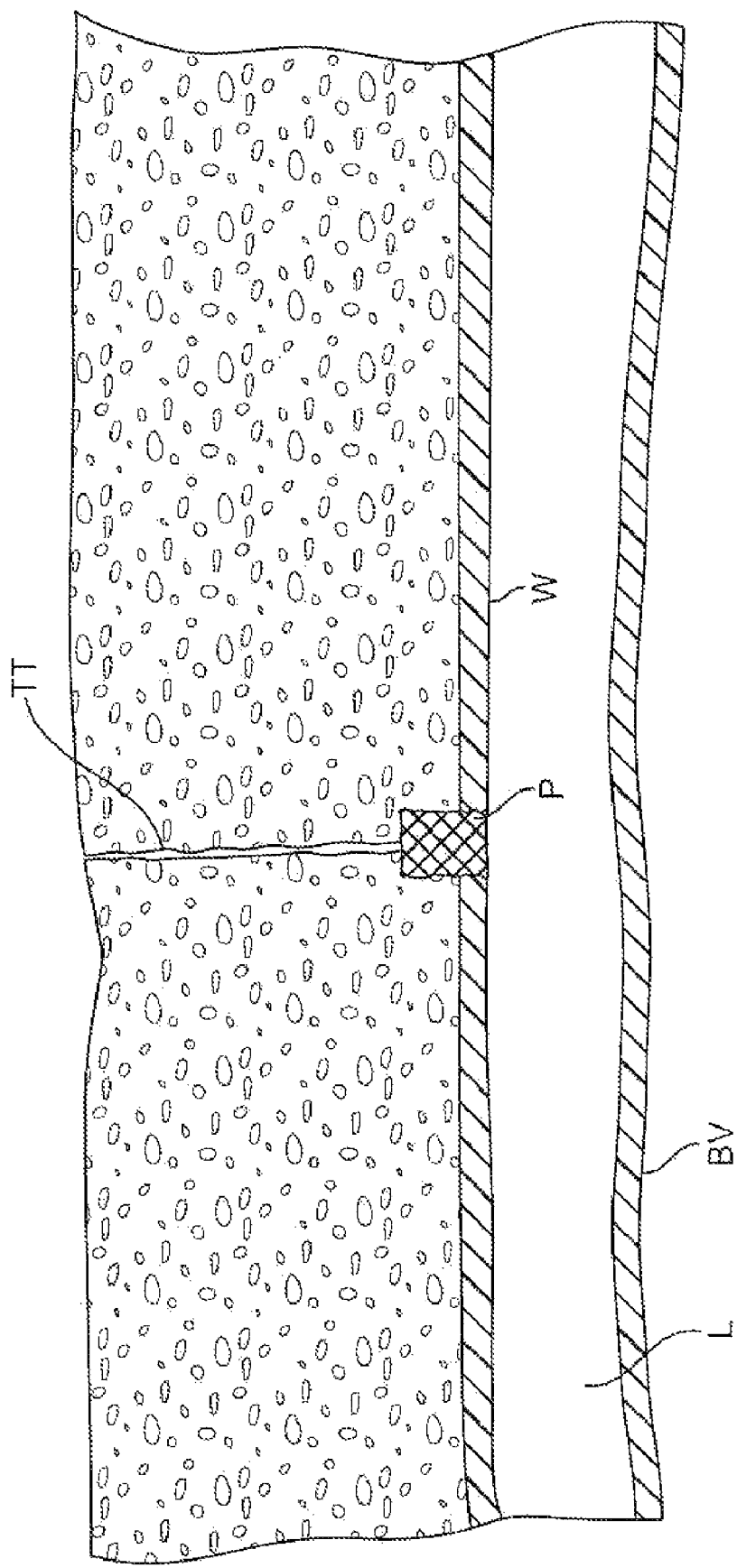

APPARATUS AND METHODS FOR CLOSING VASCULAR PENETRATIONS

CROSS-REFERENCES TO RELATED APPLICATIONS

This application is a divisional of U.S. application Ser. No. 10/795,019 filed Mar. 3, 2004, which claims the benefit of U.S. Provisional Application No. 60/452,037, filed on Mar. 4, 2003, the full disclosures of each which are incorporated herein by reference.

BACKGROUND OF THE INVENTION

1. Field of the Invention

The present invention relates generally to medical apparatus and methods. More particularly, the present invention relates to apparatus and methods for sealing a blood vessel penetration disposed at the end of a tissue tract.

A number of procedures in diagnostic and interventional cardiology rely on the introduction of a catheter into a blood vessel through a penetration in a blood vessel wall disposed at the end of a tissue tract, typically accessing a femoral artery in a patient's groin. The penetration is usually created by the Seldinger technique where a needle penetration is first formed, and the penetration subsequently dilated prior to placement of an access sheath. Diagnostic and/or interventional catheters may then be advanced to the coronary arteries using a guidewire which has been introduced over the aortic arch. At the end of the procedure, the guidewires, catheters, and access sheath are removed, leaving the blood vessel penetration and tissue tract opened and in need of closure.

The most common technique for closing the vascular wall penetration is to apply pressure on the skin over the tissue tract. After a time, clotting will occur and the healing process will initiate. Reliance on the patient's own clotting mechanism, however, is complicated since most patients have been treated with heparin or other blood thinning agents to reduce the risk of clotting and embolization during the procedure itself.

A number of improvements over pressure-induced clotting have been proposed. For example, the introduction of gelatin or other bio compatible plug materials or glues have been proposed by a number of inventors, and commercial systems are available under the Vasoseal® and Angioseal® trade names. As an alternative to sealing using such plug materials, suturing the vascular penetrations has been proposed and commercialized under the Prostar® XL and The Closers™ trade names.

Of particular interest to the present invention, the application of energy at or near the site of the vascular penetration to cauterize the penetration has been proposed by several inventors. For example, U.S. Pat. No. 4,929,246, describes methods and systems for applying laser energy to thermally seal a vascular penetration site. The method and system described, however, are both costly and complex. U.S. Pat. No. 5,415,657 describes a probe which may be placed through a tissue tract and positioned by pressing against the outside wall of the blood vessel. A penetration in the wall is then cauterized by applying energy directly to the vessel wall. This method is difficult and unreliable since it is difficult to properly position the cautery surface of the device and requires a great deal of operator training. There is great risk that the cautery surface will pass outward from the tissue tract into the lumen of the blood vessel, in which case the penetration would not be sealed and there is a risk of damage to the blood vessel wall. Even when properly placed, direct heating of the vessel wall can be ineffective and risk damage to the blood vessel wall. A third approach is described in U.S. Pat. No. 5,507,744. The vascular penetration is closed and sealed using heat generated in or thermally conducted to the tissue to induce tissue fusion. Usually, forceps incorporated within the device collapse the tissue against an electrode which delivers radio frequency energy directly into the tissue. The apparatus is complicated and requires careful manipulation to properly grasp the wall and position the electrode. In at least some instances, it is necessary to remove a guidewire from the newly sealed tissue at the end of the procedure, thus risking breach of the newly formed seal. Finally, the method and device introduce significant heat into the vessel wall, risking untended injury.

For these reasons, it would desirable to provide additional and improved methods and apparatus for closing vascular penetrations at the end of tissue tracts formed for vascular access. Such methods and apparatus should be easy to use, create reliable tissue tract closure, minimize or eliminate the risk of injury or damage to the blood vessel wall or other portions of the tissue, in general overcome the deficiencies of the prior art noted above. At least some of these objectives will be met by the invention described hereinbelow.

2. Description of the Background Art

Devices for applying energy to close blood vessels and vascular penetration are described in U.S. Pat. Nos. 4,929,246; 5,415,657; 5,507,744; and 6,077,261. Devices for closing vascular penetrations by deploying a closure assembly and delivering a sealant behind the closure assembly are described in U.S. Pat. Nos. 5,782,860; 5,922,009; 5,951,589; 6,045,570-; and 6,056,769.

BRIEF SUMMARY OF THE INVENTION

The present invention overcomes the problems of the prior art by employing a fundamentally different approach for energy-mediated blood vessel penetration closure. Instead of cauterizing, injuring, and/or deforming the blood vessel wall or surrounding tissue, the present invention provides methods and apparatus for creating a blood pool near the vascular end of the tissue tract. Energy is delivered into the blood pool to raise the temperature of the blood, to as high as 100° C., in order to induce desiccation and formation of a plug from the desiccated blood. The energy is directed and controlled to avoid injury to the blood vessel wall and surrounding tissue, and such energy-enhanced plug formation can be effective even in highly anti-coagulated blood.

In a first specific aspect of the present invention, apparatus for sealing a blood vessel penetration disposed at the end of the tissue tract comprise a shaft or other body member having a proximal end and a distal tip. The shaft is configured to advance through the tissue tract and comprises a locator for positioning the distal tip proximal of the blood vessel penetration by a predetermined distance. That is, the distal tip of the shaft will be spaced back from the blood vessel lumen so that a "plug formation region" is formed between the distal tip and the blood vessel lumen. The clotting region will be filled with relatively quiescent blood, and a means is provided at or near the distal tip of the shaft for desiccating the blood pool created by the shaft. The means will typically provide for the delivery of radiofrequency energy, heat energy, ultrasonic energy, optical energy, or the like, to the blood pool.

In a preferred embodiment of the apparatus, an anchor will be provided on the shaft for retaining the shaft at the position determined by the locator. The anchor can hold the shaft in the position determined by the locator, thus permitting withdrawal of the locator before or after plug formation has been induced, preferably before so that no portion of the apparatus is present within the plug during or after desiccation. The anchor may comprise a surface which engages skin surrounding an anterior opening of the tissue tract, for example, being a block or other structure slidably disposed on and selectively fixed to the shaft. Alternatively, the anchor may comprise an expandable member on the shaft and/or tissue-penetrating elements which may be laterally advanced from the shaft onto or into a sidewall of the tissue tract after the shaft has been located. A variety of other anchoring mechanisms will also be available.

In still further preferred embodiments of the apparatus, the locator may comprise an expandable element on the shaft which is deployable within the blood vessel lumen so that the distal tip of the shaft may be positioned by pulling back the shaft to engage the locator against an inside wall of the blood vessel. Such "tactile" positioning of the distal end of the shaft is usually performed blind, i.e., without fluoroscopic, ultrasonic, or other imaging, thus enhancing the simplicity of the procedure. Exemplary locator structures include pre-shaped wires which may be maintained in a generally straight configuration within the shaft and deployed a planar coil or other geometry which extends laterally from the distal end of the shaft. The planar coils and other locator structures will usually be disposed perpendicularly to the shaft when advanced from the shaft. Alternatively, the planar structures could be inclined at an angle from the shaft which is complementary to the angle of the tissue tract. Usually, however, it will be sufficient that the planar structure is sufficiently resilient to accommodate any angle between the tissue tract and femoral artery.

Optionally, any of these locator structures could be covered by or enveloped within a membrane to help provide temporary hemostasis before RF energy is applied. Alternatively, the diameter of the shaft immediately proximal to the expandable locator may be sized to seal against the vessel wall penetration to provide temporary hemostasis.

A scale, stop, or other measuring or positioning mechanism will typically be provided so that when the shaft is pulled back to engage the locator against the interior of the luminal wall, the distal tip of the shaft may be properly positioned away from the luminal wall, typically by a distance in the range from 1. mm to 10 mm, preferably from 2 mm to 6 mm. These distances have found to provide the optimum blood pool volume for inducing clotting by the application of energy according to the present invention. In addition to the wire locator structured, as described, the present invention could rely on a variety of other expansible structures for engaging the interior wall of the blood vessel. For example, malecots, wire arrays, expandable meshes, and other structures which permit the passage of blood into the blood pool will also be useful.

Methods according to the present invention for sealing a blood vessel penetration disposed at a distal end of a tissue tract comprise introducing a sealing device through the tissue tract. The distal tip of the sealing device is positioned at a predetermined distance proximal to the distal end of the tissue tract, typically in the range from 1 mm to 10 mm, preferably from 2 mm to 6 mm, to form a desiccation region between the distal tip of the device and the distal end of the tissue tract. Desiccation is induced in a blood pool located in the desiccation region to form a plug which seals the tissue tract to inhibit bleeding and allows natural healing of the tissue tract, usually without the need to apply external pressure as is commonly done at present.

The sealing device is preferably positioned by deploying a locator from the device in a lumen of the blood vessel. The device is pulled back to engage a locator against an inner wall of the blood vessel, thus tactilely positioning the device. Usually, the device will have been introduced over the guidewire which was used in the interventional or diagnostic procedure for which the blood vessel penetration was formed. Usually, the guidewire will be removed, optionally by exchange with the locator which is used to position the device once it is generally in place within the tissue tract. The locator is preferably an expansible element, as generally described above in connection with the apparatus of the present invention, and is expanded within the blood vessel lumen after being passed through the sealing device. After properly positioning the sealing device, the device is anchored in place within the tissue tract. Anchoring can be accomplished by fixing the shaft to a surface which is engaged against the skin surrounding the tissue tract. Optionally the surface may also comprise a protective skin guard to inhibit any unintended heating or damage to the skin. Alternatively, anchoring may comprise penetrating elements from the device into tissue surrounding the tissue tract. In another case, the locator is preferably, although not necessarily, removed after anchoring of the sealing device and before inducing desiccation in the blood pool. By removing the locator prior to desiccation, the plug will be formed without the locator or any other portions of the sealing device present within the plug to interfere with clot formation or disturb the plug by removing the elements after the plug is formed.

Desiccation is usually induced by applying energy to the blood pool defined between the distal end of the sealing device and the luminal wall. Exemplary forms of energy which may be applied include heat, radiofrequency energy, ultrasound, and laser or other forms of optical energy. Alternatively or additionally, desiccation may be accompanied by release of a clotting factor or other clotting agent into the blood pool from the sealing device. The present invention, however, relies primarily on blood desiccation, not clotting, to cause plug formation and sealing of the blood vessel penetration.

The methods and devices of the present invention may be modified in a variety of ways to achieve different effects. For example, a blade or other mechanism may be provided to remove desiccated or charred blood from the electrode or other energy-applying surface of the device. The device may also be provided as part of a kit including the introducer or access sheath which is used to provide initial access. In some cases, the access sheath can be modified to cooperate with the sealing device, e.g., by providing energy-conductive and/or energy-insulating surfaces to help control and direct energy transmission. The energy delivery surface of the sealing device might also be modified to translate the surface back through the blood pool to enhance heat and energy transfer. Other modifications may also be made without departing from the scope of the present invention.

BRIEF DESCRIPTION OF THE DRAWINGS

FIGS. 4A-4F illustrate use of the apparatus of FIG. 1 for performing a method according to the principles of the present invention.

DETAILED DESCRIPTION OF THE INVENTION

Apparatus for sealing blood vessel penetrations according to the present invention include a shaft or other body configured to be advanced through a tissue tract, a locator positionable on, in, or otherwise with the shaft to properly position a distal end of the shaft relative to the blood vessel lumen, and means on the shaft for inducing desiccation when the distal end of the shaft is properly positioned in the tissue tract. Usually, an anchor or anchoring mechanism will also be provided on, in, or together with the shaft for holding the shaft in place once it has been positioned with the locator. Three specific apparatus embodiments including each of these components are illustrated in FIGS. 1-3.

Figure 1:
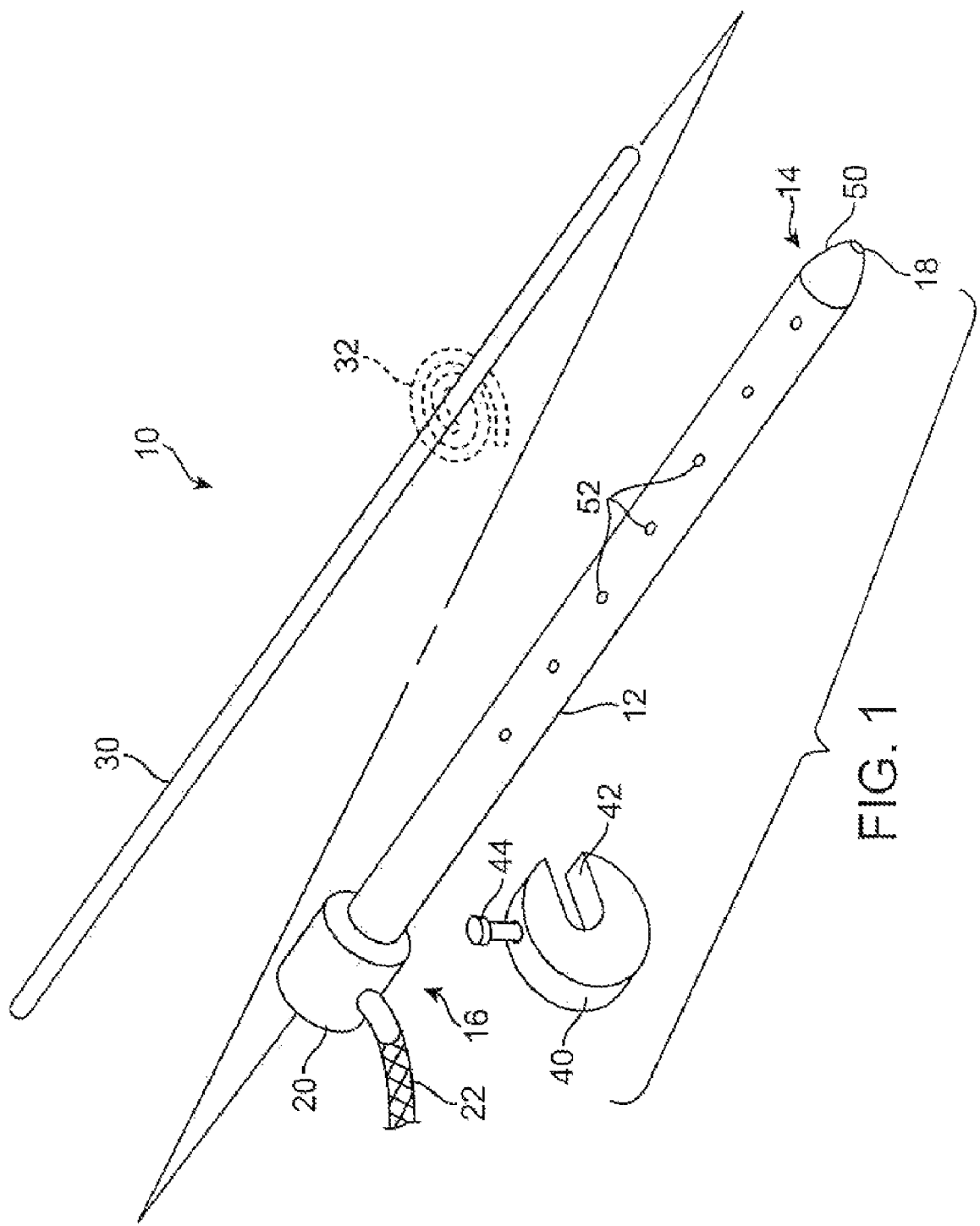
FIG. 1 illustrates a first embodiment of the apparatus for sealing a blood vessel penetration constructed in accordance with the principles of the present invention.

Referring to FIG. 1, a first embodiment 10 of the apparatus constructed in accordance with the principles of the present invention comprises a shaft 12 having a distal end 14, a proximal end 16 and at least one lumen (not visible) therethrough which terminates in a distal opening 18. The housing 20 is secured at the proximal end 16 of the shaft 12 and includes an electrical connecting cable 22. A wire 30 which is positionable through the lumen of shaft 12 is composed of a metal or other material having an elastic memory so that at least a distal end thereof may be elongated or radially constrained into a straightened configuration (as shown in full line) that will return to a planar coil 32 or other laterally expanded configuration (as shown in broken line in FIG. 1). The embodiment 10 further comprises an external anchor 40 having an opening 42 which may be placed over the exterior of shaft 12 and a set screw 44 which permits selective locking of the anchor 40 in any position along the length of the shaft 12. A distal tip 50 of the shaft 12 is adapted to deliver electrical, heat, optical, or other forms of energy in a distal direction relative to the shaft, typically being an electrode for delivering radio frequency electrical energy. Optionally, a plurality of one or more thermocouples 52 or other temperature sensors may be provided along the length of the shaft at varying distances from the distal tip.

The length and diameter of the shaft will be selected to permit passage and deployment into tissue tracts which are formed to provide vascular access for various intravascular diagnostic and therapeutic techniques, such as angiography, angioplasty, minimally invasive cardiac surgeries, and the like. The length of the shaft will typically be in the range from 5 cm to 25 cm, preferably being from 6 cm to 15 cm. The diameter (or width in the case of non-circular cross-sections) of the shaft 12 will typically be in the range from 1 mm to 6 mm, preferably from 2 mm to 4 mm. The distal end 14 is shown as being a generally dome-shaped, but could be other configurations, including flat, conical, hemispherical, or the like. The shaft 12 will generally be composed of an electrically and thermally non-conductive material, typically being a polymer, reinforced polymer, or the like. As the distal element 50 will typically be electrically or thermally active, it is highly desirable to insulate the shaft against the transmission of both electricity and heat upward into the tissue tract. Optionally, a skin guard or other protective device may be provided on the anchor 40 to extend at least partially into the tissue tract and isolate the exterior of the shaft from the exposed tissue.

Figure 2:
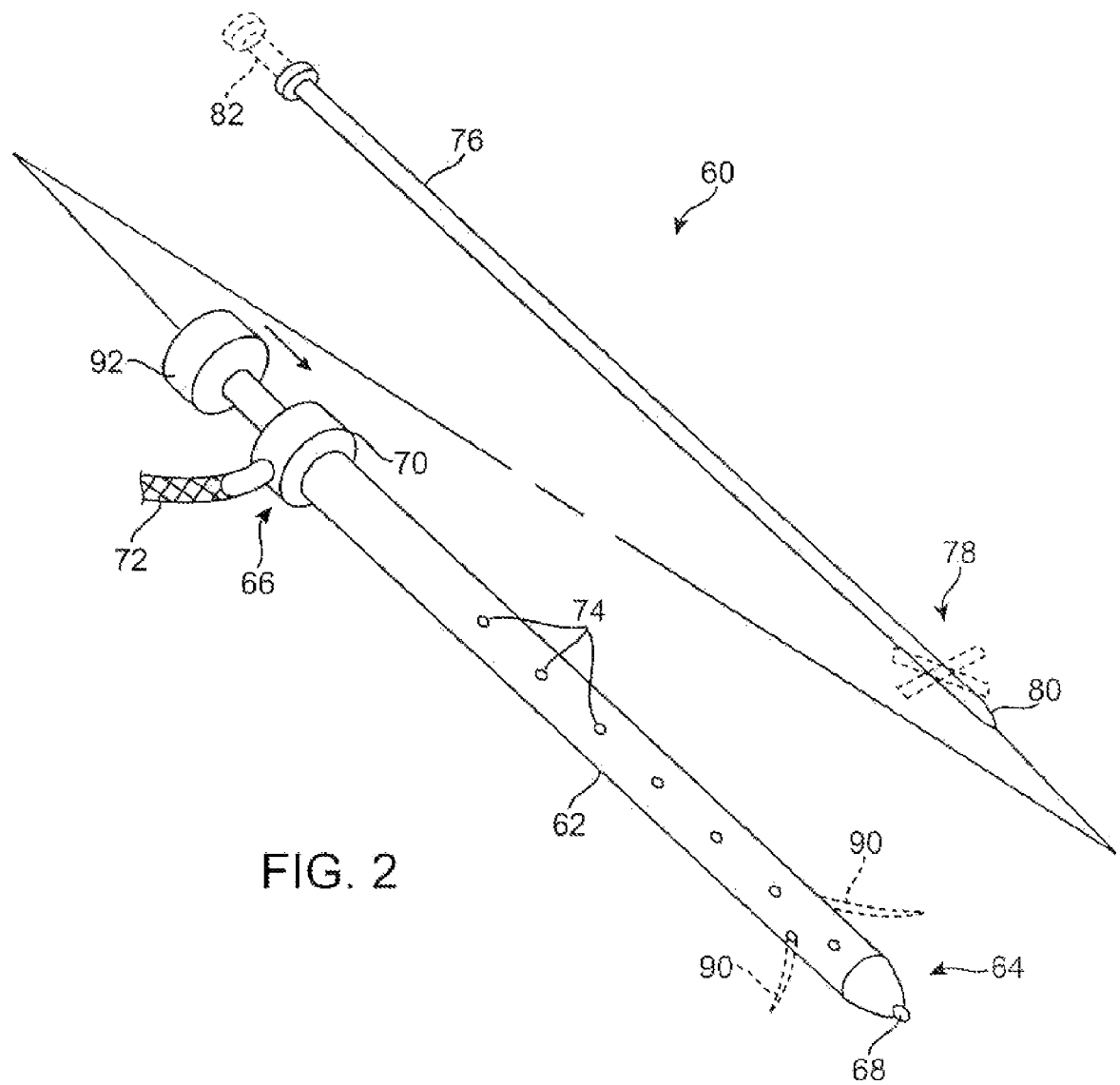
FIG. 2 illustrates a second embodiment of an apparatus for sealing a blood vessel penetration constructed in accordance with the principles of the present invention.
Figure 3:
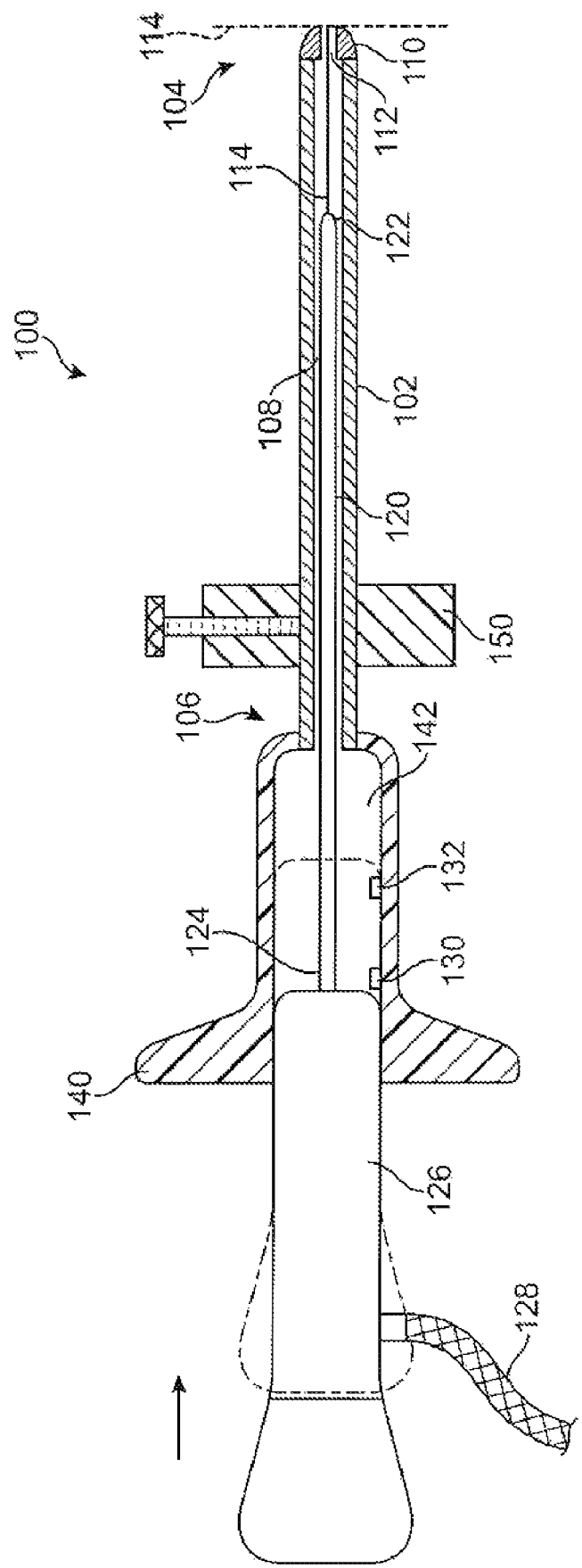
FIG. 3 illustrates a third embodiment of an apparatus for sealing a blood vessel penetration constructed in accordance with the principles of the present invention.

An alternative embodiment 60 of the apparatus according to the present invention is illustrated in FIG. 2. Apparatus 60 also includes a shaft 62 which has a distal end 64, a proximal end 66, and a central lumen therethrough (not shown) terminating in a distal port 68. Proximal housing 70 includes an electrical connecting cable 72 and, optionally, one or more thermocouples or other temperature sensors 74 may be provided along the length of the shaft.

Apparatus 60 differs from apparatus 10, however, in the nature of the locator and the anchor. A locator 76 of apparatus 60 is generally formed as a wire having an expandable malecot structure 78 at its distal end 80. The malecot may be deployed laterally upwardly (as shown in broken line) by pulling on a cable or other filament 82 which runs coaxially through the wire 76, shown in broken line. Malecot structures for engaging tissue and stabilizing medical device components are well know in the art and need not be described further herein.

The anchor mechanism of apparatus 60 comprises one or more tissue-penetrating elements 90, typically needles, which may be selectively advanced laterally into tissue surrounding the tissue tract by pushing in a distal direction on a plunger 92 which is connected to push the penetrating elements into the extended configuration shown in broken line in FIG. 2.

A third embodiment 100 of the apparatus of the present invention is illustrated in FIG. 3. The apparatus 100 comprises a shaft 102 having a distal end 104, a proximal end 106, and a lumen 108 extending from the distal end to the proximal end. The shaft 102 will have the dimensions and be composed of the materials generally described above. An electrode structure 110 is disposed at the distal end of the shaft 102 and has an axial passage 112 therethrough which is open to the lumen 108. A locator wire 114 is disposed in the distal end of lumen 108 and extends into the axial passage 112 so that it may be reciprocated between an axially straight configuration (as shown in full line) and a laterally deployed configuration which extends through the passage 112, as shown in broken line. It will be appreciated that the locator may be deployed within a blood vessel lumen for locating the shaft 102 in the manner described above for the other embodiments.

The wire 114 is deployed by a rod 120 which is connected at a distal end 122 to the wire 114 and at a proximal end 124 to a slider 126. An electric cable 128 is attached to the slider and internally connected to the distal electrode tip 110 and to a pair of position sensors 130 and 132. The slider 126 is positioned within a handle 140 which has cavity 142 for slidably receiving the handle 126. Thus the slider 126 may be moved between a proximally retracted configuration (shown in solid line) where the wire 114 is straightened and collapsed within the shaft lumen 108 and distally advanced position (shown in broken line) where the wire 114 is laterally deployed (also shown in broken line). An external anchor 150 is provided for selective attachment to the shaft 102 so that the shaft may be anchored and located once the distal 104 is properly positioned within a tissue tract using the locator wire 114. The position sensors 130 and 132 provide feedback of the locator wire position 114. When both sensors 130 and 132 detect the slider 126, the operator will receive a signal that the locator has been deployed and pulled back properly to provide the desired set-back distance from the vessel lumen. Usually, an interlock will be provided in the associated power supply (not shown in FIG. 3) to prevent energy delivery unless the sensors 130 and 132 confirm that the wire 114 has been withdrawn from the blood pool.

Figure 4A:
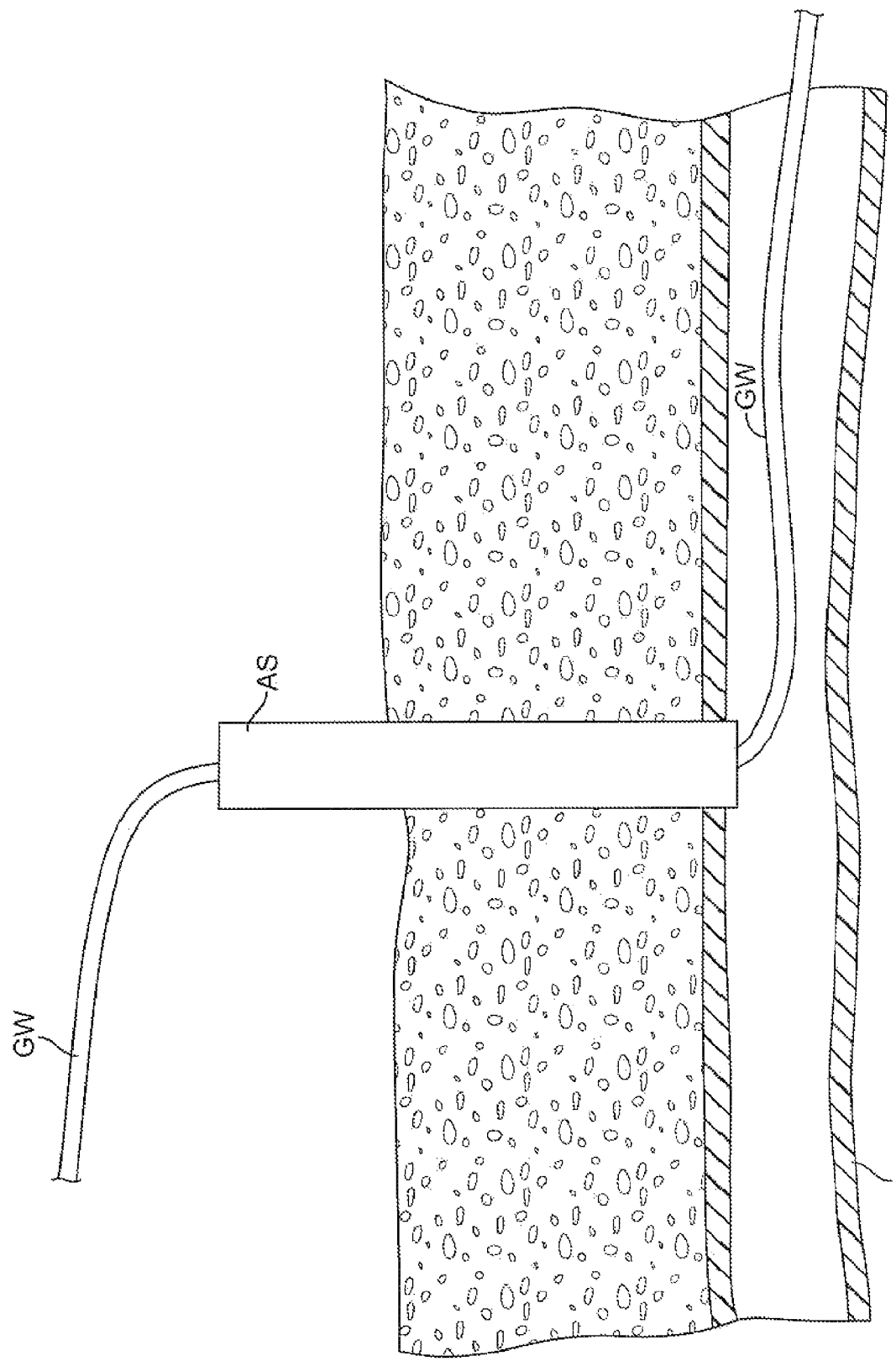

Use of the apparatus of the present invention for sealing a blood vessel penetration is described in connection with FIGS. 4A-4F. Usually, the procedures will begin after all diagnostic and interventional catheters have been removed and the patient is left with an access sheath AS and guidewire GW in place, as shown in FIG. 4A. Optionally, if a sheath is used, the guidewire GW may be unnecessary. Note that the access sheath is shown as being in a generally vertical or perpendicular orientation relative to the blood vessel BV which is being accessed. In the case of the femoral artery in the groin, the access sheath will often be inclined at an angle relative to the blood vessel and blood vessel lumen. For ease of explanation, however, the drawings will show the vertical perpendicular access. It will be appreciated that the shapes and orientations of the locator, in many cases, may be optimized in order to accommodate the non-vertical orientation of the access sheath and tissue tract, and the present invention will encompass all such variations.

Figure 4B:
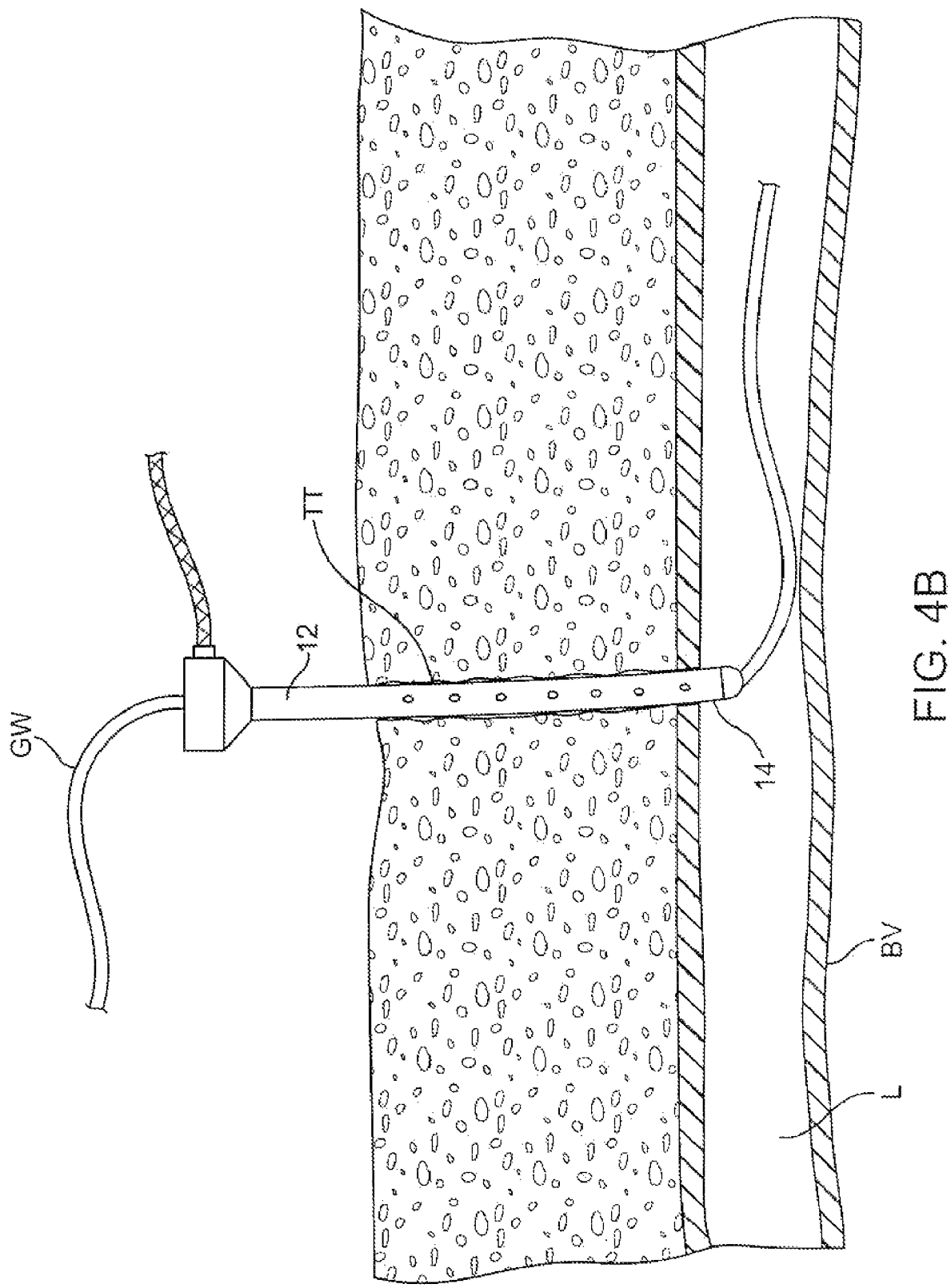
Figure 4C:
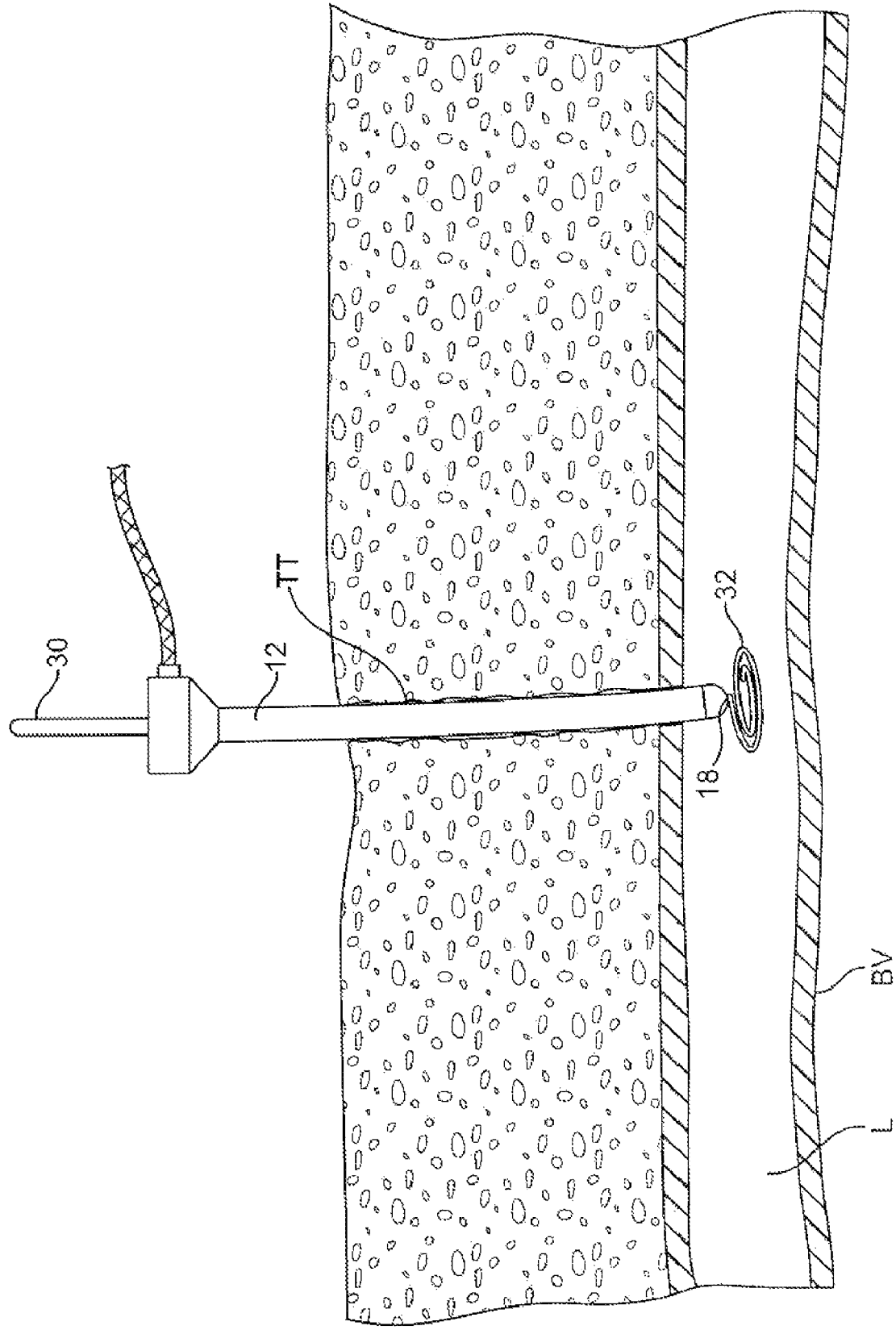

The first step of the method of the present invention is shown in FIG. 4B. After removing access sheath AS, shaft 12 of device 10 may be introduced through the tissue tract TT until the distal 14 is disposed in the blood vessel lumen L over the guidewire GW. The guidewire may then be removed and exchanged with the locator wire 30 which is advanced through the shaft lumen and out of the distal port 18 to deploy the planar coil 32 within the blood vessel lumen L, as shown in FIG. 4C. The shaft 12 is then pulled back (proximally) through the tissue tract TT so that the planar coil 32 is engaged against the inner wall W of the blood vessel lumen L as shown in FIG. 4D. The shaft will be pulled back so that the distal tip 14 is a preselected distance from the wall W, typically in the ranges set forth above. This distance may be determined by locking a proximal portion of the wire 30 relative to the shaft 12 so that the shaft is properly positioned when the user feels resistance to pulling which results from the engagement of the planar coil 32 against the wall W. Alternatively, the wire 32 may be positioned first, independently of the shaft 12, and the shaft then positioned based on a scale or other measurement apparatus provided on the wire 30. In another case, before proceeding to the next step, it is essential that the distal end 14 of the shaft 12 be positioned back from the wall W by the desired distance in order to create a blood pool BP in the region between the distal tip and the blood vessel lumen L, as shown in FIG. 4D.

Figure 4E:
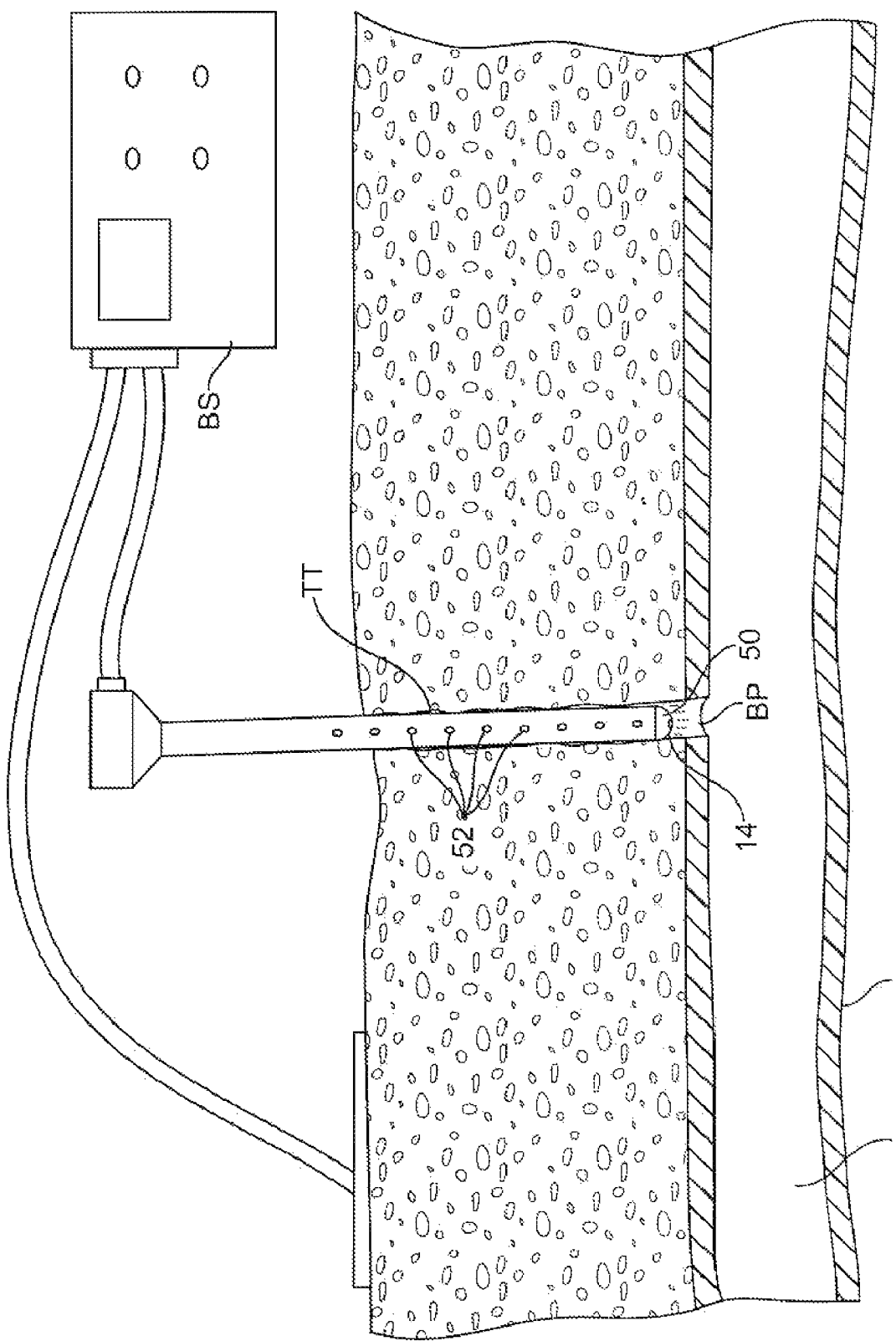

After the shaft 12 has been properly positioned, the wire 30 may be withdrawn, as shown in FIG. 4E, and energy applied through the electrode or other energy applying surface 50. Typically, this is done by connecting the device to a power supply PS, for example, a radio frequency power supply, which delivers energy to the element 50. In the case of radio frequency, preferred frequencies are in the range from 350 kHz to 2 MHz that powers in the range from 5 watts to 100 watts, usually from 5 watts to 50 watts. As illustrated, the radiofrequency power supply PS operates with a "monopolar" protocol where one pole is attached to the electrode 50 and the other pole to a dispersive pad P placed externally on the patient's skin, preferably on an opposite side of the leg being treated. Optionally, while energy is being delivered, the temperature sensors 52 may be monitored to assure that no unintended tissue heating along the tissue tract TT occurs. Temperature feedback may optionally be used to control energy delivery to the blood pool. Further optionally, impedance through the blood pool may be monitored to determine when desiccate is complete based upon an observed rise in impedance.

After the procedure has been completed, the shaft 12 is withdrawn, allowing the tissue tract to collapse over the newly formed plug which is directly over the blood vessel wall W.

While the above is a complete description of the preferred embodiments of the invention, various alternatives, modifications, and equivalents may be used. Therefore, the above description should not be taken as limiting the scope of the invention which is defined by the appended claims.

What is claimed is:

1. Apparatus for sealing a blood vessel penetration disposed at the end of a tissue tract, said apparatus comprising:
   a shaft having a proximal end and a distal tip, said shaft being configured to advance through the tissue tract;
   a locator on the shaft for positioning the distal tip a predetermined proximal distance from the blood vessel penetration; and
   means on the distal tip of the shaft for delivering energy to induce clotting in a blood pool located in the tissue tract distally of the distal tip when the tip is positioned by the locator.

2. Apparatus as in claim 1, wherein the predetermined distance is in the range from 1.25 mm to 6.35 mm.

3. Apparatus as in claim 1, further comprising an anchor on the shaft, wherein the anchor is deployable to retain the shaft at the position determined by the locator after the locator has been withdrawn.

4. Apparatus as in claim 3, wherein the anchor comprises tissue penetrating elements which are laterally advanceable from the shaft into a side wall of the tissue tract after the shaft has been located.

5. Apparatus as in claim 1, wherein the locator comprises an expandable element which is deployable within the blood vessel lumen so that the distal tip is positioned by pulling back the shaft to engage the locator against an inside wall of the blood vessel.

6. Apparatus as in claim 5, wherein the expandable element comprises a wire which is straightened when constrained in the shaft and which expands when advanced into the blood vessel lumen.

7. Apparatus as in claim 6, wherein the wire forms a planar coil disposed perpendicularly to the axis of the shaft when advanced from the shaft.

8. Apparatus as in claim 3, wherein the anchor comprises a surface which engages skin surrounding an opening to the tissue tract, wherein the surface can be selectively attached to the shaft after the shaft has been located.

9. Apparatus as in claim 1, wherein the energy delivering means comprises an electrode, a heated surface, a fiberoptic waveguide, or an ultrasonic transducer.

* * * * *